(12) United States Patent
Meglan et al.

(10) Patent No.: US 12,262,863 B2
(45) Date of Patent: Apr. 1, 2025

(54) SYSTEMS AND METHODS FOR IMAGE MAPPING AND FUSION DURING SURGICAL PROCEDURES

(71) Applicant: Covidien LP, Mansfield, MA (US)

(72) Inventors: Dwight Meglan, Westwood, MA (US); Meir Rosenberg, Newton, MA (US)

(73) Assignee: Covidien LP, Mansfield, MA (US)

( * ) Notice: Subject to any disclaimer, the term of this patent is extended or adjusted under 35 U.S.C. 154(b) by 170 days.

(21) Appl. No.: 17/911,239

(22) PCT Filed: May 12, 2021

(86) PCT No.: PCT/US2021/031886
§ 371 (c)(1),
(2) Date: Sep. 13, 2022

(87) PCT Pub. No.: WO2021/231508
PCT Pub. Date: Nov. 18, 2021

(65) Prior Publication Data
US 2023/0099835 A1 Mar. 30, 2023

Related U.S. Application Data

(60) Provisional application No. 63/023,435, filed on May 12, 2020.

(51) Int. Cl.
*A61B 1/00* (2006.01)
*A61B 1/04* (2006.01)
(Continued)

(52) U.S. Cl.
CPC ...... *A61B 1/00006* (2013.01); *A61B 1/00009* (2013.01); *A61B 1/0005* (2013.01);
(Continued)

(58) Field of Classification Search
CPC ............ A61B 1/00006; A61B 1/00009; A61B 1/0005; A61B 1/045; A61B 1/046;
(Continued)

(56) References Cited

U.S. PATENT DOCUMENTS 6,132,368 A 10/2000 Cooper
6,206,903 B1 3/2001 Ramans
(Continued)

FOREIGN PATENT DOCUMENTS

WO 2013025530 A1 2/2013

OTHER PUBLICATIONS

International Search Report mailed May 11, 2021 and Written Opinion completed Sep. 1, 2021 corresponding to counterpart Int'l Patent Application PCT/US2021/031886.

*Primary Examiner* — Bo Joseph Peng
(74) *Attorney, Agent, or Firm* — Carter, DeLuca & Farrell LLP

(57) ABSTRACT

A method for mapping and fusing endoscopy images includes capturing a first image of an object within a surgical operative site, by a first imaging device; and capturing a second image of the object, by a second imaging device. The first image includes the first light radiating from the object, and a first reference point. The second image includes the second light radiating from the object, and a second reference point. The method further includes comparing a first location of the first reference point in the first image to a second location of the second reference point in the second image, determining a relative pose of the first imaging device to the second imaging device based on the comparing, generating an augmented image fusing the first image and the second image based on the determined relative pose, and displaying the augmented image on a display.

9 Claims, 5 Drawing Sheets

(51) Int. Cl.
 *A61B 1/045* (2006.01)
 *A61B 1/06* (2006.01)
 *A61B 34/20* (2016.01)
 *A61B 90/90* (2016.01)
 *G06T 7/521* (2017.01)
 *G06T 7/70* (2017.01)

(52) U.S. Cl.
 CPC .............. *A61B 1/045* (2013.01); *A61B 1/046* (2022.02); *A61B 1/0638* (2013.01); *A61B 34/20* (2016.02); *A61B 90/90* (2016.02); *G06T 7/521* (2017.01); *G06T 7/70* (2017.01); *A61B 2034/2065* (2016.02); *G06T 2207/10028* (2013.01); *G06T 2207/10068* (2013.01); *G06T 2207/20221* (2013.01); *G06T 2207/30004* (2013.01)

(58) Field of Classification Search
 CPC ....... A61B 1/0638; A61B 34/20; A61B 90/90; A61B 2034/2065; G06T 7/521; G06T 7/70; G06T 2207/10028; G06T 2207/10068; G06T 2207/20221; G06T 2207/30004
 See application file for complete search history.

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |

(56) References Cited

U.S. PATENT DOCUMENTS

| | | |
|---|---|---|
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,165,976 B2 | 1/2019 | Shachaf et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |

(56) References Cited

U.S. PATENT DOCUMENTS

| | | |
|---|---|---|
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2012/0207401 A1 | 8/2012 | Archer |
| 2013/0070989 A1 | 3/2013 | Hyde et al. |
| 2019/0201104 A1 | 7/2019 | Shelton, IV et al. |

SYSTEMS AND METHODS FOR IMAGE MAPPING AND FUSION DURING SURGICAL PROCEDURES

CROSS-REFERENCE TO RELATED APPLICATIONS

The present application is a U.S. National Stage Application filed under 35 U.S.C. § 371 (a) claiming the benefit of and priority to International Patent Application No. PCT/US2021/031886, filed May 12, 2021, which claims the benefit of and priority to U.S. Provisional Patent Application Ser. No. 63/023,435, filed May 12, 2020, the entire disclosures of each of which being incorporated by reference herein.

FIELD

The present disclosure relates to devices, systems, and methods for mapping and fusing images from multiple sources, and more particularly, to the fusing of images from multiple sources during surgical procedures.

BACKGROUND

Robotic surgical systems such as teleoperative systems are used to perform minimally invasive surgical procedures that offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a stapler, an electrosurgical instrument, etc., in response to movement of input devices by a surgeon viewing images captured by the image capturing device of a surgical site. During a robotic surgical procedure, each of the tools is inserted through an opening, either natural or an incision, into the patient and positioned to manipulate tissue at a surgical site. The openings are placed about the patient's body so that the surgical instruments may be used to cooperatively perform a robotic surgical procedure, and the image capturing device may view the surgical site.

During a robotic surgical procedure, it is important to accurately know and control the position of the tools within the surgical site. Accordingly, there is a continuing need for systems and methods for mapping and fusing images of a surgical site from multiple image sources during robotic surgical procedures.

SUMMARY

The disclosure relates to devices, systems, and methods for fusing images from multiple sources during surgical procedures. In accordance with aspects of the disclosure, a system for object identification in endoscopy images is presented. The system includes a light source, a first imaging device, a second imaging device, and an imaging device control unit. The light source is configured to provide light within a surgical operative site.

In an aspect of the present disclosure, a system for mapping and fusing endoscopy images includes a light source configured to provide light within a surgical operative site, a first imaging device configured to acquire images from the surgical operative site, a second imaging device configured to acquire images from the surgical operative site, a display, and an imaging device control unit configured to control the first imaging device and the second imaging device. The light source configured to produce a first light including an infrared (IR) band and a second light configured to produce a visible band. The control unit includes a processor and a memory with instructions stored thereon. The instructions, which, when executed by the processor, cause the system to capture a first image of an object within a surgical operative site, by the first imaging device, the image including the first light radiating from the object, and a first reference point; capture a second image of the object, by the second imaging device, the image including the second light radiating from the object, and a second reference point; compare a first location of the first reference point in the first image to a second location of the second reference point in the second image; determine a relative pose of the first imaging device to the second imaging device based on the comparing; generate an augmented image fusing the first image and the second image based on the determined relative pose; and display the augmented image on the display.

In an aspect of the disclosure, the light source may be configured to produce a first light including an infrared (IR) band and a second light configured to produce a visible band.

In another aspect of the disclosure, the first reference point may include a structured light, and wherein the second reference point includes a structured light.

In yet another aspect of the disclosure, generating the augmented image may further include determining a virtual imaging device viewpoint. Generating the augmented image may be further based on the virtual imaging device viewpoint.

In a further aspect of the disclosure, generating the augmented view may further include determining a first optical path distortion of the first imaging device and a second optical path distortion of the second imaging device, and processing the first image based on the first optical path distortion to match the second optical path distortion.

In an aspect of the disclosure, the instructions, when executed, may further cause the system to perform tracking of the object based on the first reference point and the second reference point.

In a further aspect of the disclosure, the first reference point and the second reference point may include a logo, a QR code, a texture, a dot pattern, and/or a unique identifier.

In yet another aspect of the disclosure, the first image may include a first distance information for each pixel of the first image. The second image may include a second distance information for each pixel of the second image. The relative pose of the first imaging device may be further based on the first distance information and the second distance information.

In a further aspect of the disclosure, the generating the augmented image further includes a portion of the first image which includes the object to represent the object in the augmented image, and a remaining portion of the augmented image includes a fusion of the first image and the second image.

In accordance with aspects of the disclosure, a method for mapping and fusing endoscopy images is presented. The method includes capturing a first image of an object within a surgical operative site, by a first imaging device; and capturing a second image of the object, by a second imaging device. The first image includes the first light radiating from the object, and a first reference point. The second image includes the second light radiating from the object, and a second reference point. The method further includes comparing a first location of the first reference point in the first image to a second location of the second reference point in the second image, determining a relative pose of the first imaging device to the second imaging device based on the comparing, generating an augmented image fusing the first image and the second image based on the determined relative pose, and displaying the augmented image on a display.

In yet a further aspect of the disclosure, the first light may include an infrared (IR) band, and the second light includes a visible band.

In yet another aspect of the disclosure, the first reference point may include structured light, and the second reference point may include a structured light.

In a further aspect of the disclosure, generating the augmented image may further include determining a virtual imaging device viewpoint. Generating the augmented image may be further based on the virtual imaging device viewpoint.

In yet another aspect of the disclosure, generating the augmented view may further include determining a first optical path distortion of the first imaging device and a second optical path distortion of the second imaging device and processing the first image based on the first optical path distortion to match the second optical path distortion.

In a further aspect of the disclosure, the method may further comprise performing tracking of the object based on the first reference point and the second reference point.

In an aspect of the disclosure, the first reference point and the second reference point may include a logo, a QR code, a texture, a dot pattern, and/or a unique identifier.

In accordance with aspects of the disclosure, the first image may include a first distance information for each pixel of the first image.

The second image may include a second distance information for each pixel of the second image. The relative pose of the first imaging device may be further based on the first distance information and the second distance information.

In a further aspect of the disclosure, the generating the augmented image may further include only using a portion of the first image, which includes the object to represent the object, and a remaining portion of the augmented image includes a fusion of the first image and the second image.

In yet another aspect of the disclosure, the first imaging device and the second imaging device may include a stereographic imaging device.

In accordance with aspects of the disclosure, a non-transitory storage medium that stores a program causing a computer to execute a computer-implemented method for mapping and fusing endoscopy images is presented. The method includes capturing a first image of an object within a surgical operative site, by a first imaging device; and capturing a second image of the object, by a second imaging device. The first image includes the first light radiating from the object, and a first reference point. The second image includes the second light radiating from the object, and a second reference point. The method further includes comparing a first location of the first reference point in the first image to a second location of the second reference point in the second image, determining a relative pose of the first imaging device to the second imaging device based on the comparing, generating an augmented image fusing the first image and the second image based on the determined relative pose, and displaying the augmented image on a display.

In accordance with aspects of the disclosure, a system for mapping and constructing a 3D model, includes a display, a light source configured to provide light within a surgical operative site, a first imaging device configured to acquire images from the surgical operative site, a second imaging device configured to acquire images from the surgical operative site, and an imaging device control unit configured to control the first imaging device and the second imaging device. The control unit includes a processor and a memory storing instructions thereon, which, when executed by the processor, cause the system to capture a first image of an object within a surgical operative site, by the first imaging device, and capture a second image of the object, by the second imaging device, segment the first image to extract a known reference object, determine a first relative location of the first imaging device based on the extracted known reference object, segment the second image to extract the known reference object, determine a second relative location of the second imaging device based on the extracted known reference object; and construct a 3D model of the surgical operative site based on the determined first relative location and the determined second relative location.

In an aspect of the disclosure, the light source may be configured to produce an infrared (IR) band and/or a visible band.

In another aspect of the disclosure, the first imaging device may include a first viewpoint of the surgical operative site, and the second imaging device may include a second viewpoint of the surgical operative site different from the first viewpoint.

In yet another aspect of the disclosure, the system may further include a second light source that emits structured light to the object within the surgical operative site.

In a further aspect of the disclosure, the instructions when executed may further cause the processor when constructing the 3D model to determine a virtual imaging device location, generate a virtual viewpoint of the 3D model based on the virtual imaging device location, and display on a display the virtual viewpoint of the 3D model.

In yet another aspect of the disclosure, the virtual viewpoint mat include a stereoscopic image In yet a further aspect of the disclosure, the first imaging device may include a 2D imaging device and the second imaging device may include a stereographic imaging device.

In accordance with aspects of the disclosure, a method for mapping and constructing a 3D model includes capturing a first image of an object within a surgical operative site by a first imaging device and capturing a second image of the object by a second imaging device, segmenting the first image to extract a known reference object, determining a first relative location of the first imaging device based on the extracted known reference object, segmenting the second image to extract the known reference object, determining a second relative location of the second imaging device based on the extracted known reference object, and constructing a 3D model of the surgical operative site based on the determined first relative location and the determined second relative location.

In an aspect of the disclosure, the method may further include producing at least one of an infrared (IR) band or a visible band, by a first light source.

In another aspect of the disclosure, the first imaging device may include a first viewpoint of the surgical operative site, and the second imaging device may include a second viewpoint of the surgical operative site different from the first viewpoint.

In yet another aspect of the disclosure, the method may further include emitting a structured light to the object within the surgical operative site.

In a further aspect of the disclosure, constructing the 3D model may further include determining a virtual imaging device location, generating a virtual viewpoint of the 3D model based on the virtual imaging device location, and displaying on a display the virtual viewpoint of the 3D model.

In yet a further aspect of the disclosure, the first imaging device may include a 2D imaging device and the second imaging device may include a stereographic imaging device.

In yet another aspect of the disclosure, the virtual viewpoint mat include a stereoscopic image.

Further details and aspects of various embodiments of the disclosure are described in more detail below with reference to the appended figures.

BRIEF DESCRIPTION OF THE DRAWINGS

Embodiments of the disclosure are described herein with reference to the accompanying drawings, wherein.

Figure 1:
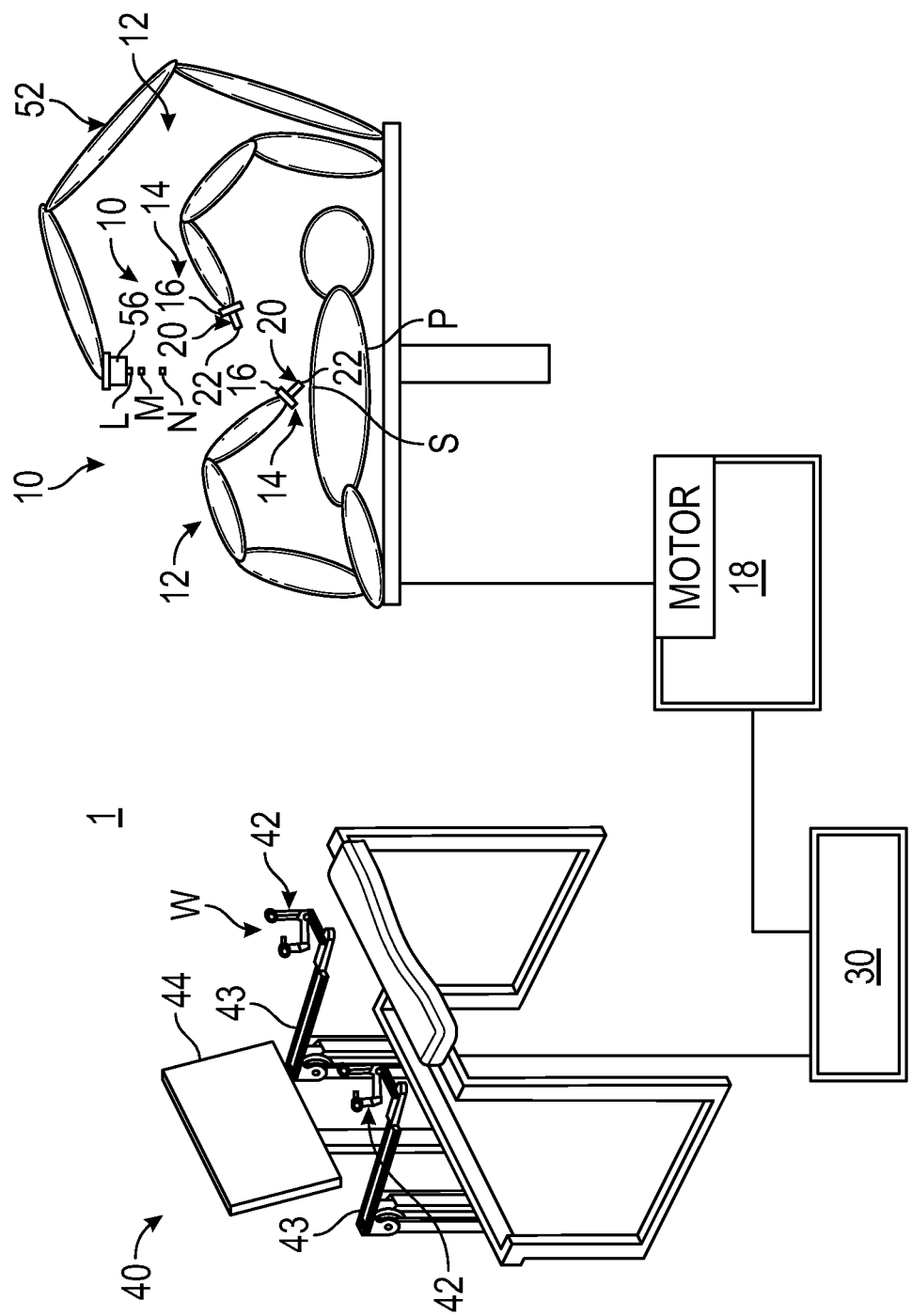
FIG. 1 is a schematic illustration of a user interface and a robotic system in accordance with the present disclosure.

Further details and aspects of exemplary embodiments of the disclosure are described in more detail below with reference to the appended figures. Any of the above aspects and embodiments of the disclosure may be combined without departing from the scope of the disclosure.

DETAILED DESCRIPTION OF EMBODIMENTS

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

The disclosure is applicable where images of a surgical site are captured. Endoscope systems are provided as an example, but it will be understood that such description is exemplary and does not limit the scope and applicability of the disclosure to other systems and procedures.

A straightforward approach to minimally invasive surgical site visualization is to use a white light endoscope, with stereoscopic imaging being particularly desirable in robotic surgery. Near-infrared fluorescence may be used to see functionally oriented images such as indocyanine green dye that shows blood perfusion. Unfortunately, these two imaging approaches are often present in two separate endoscopes such that the images are separately displayed, detracting from their intraoperative utility. It is desirable to allow these two distinct imaging approaches to be displayed together in a single fused display which provides a consistent representation of the surgical site information.

Time sequential or geometrically unique simultaneous structured light projection allows common points to be seen simultaneously in two or more endoscope views. These common spatial points across the individual scope views allow the 3D dimension surfaces seen by each endoscope to be rendered in a common coordinate frame. With these 3D surfaces known to the multiple scopes, a fused data set can be created and displayed from the most clinically appropriate point of view.

By using one or more techniques for deriving the distance that each observed pixel in an image from a camera's image sensor in a manner that allows common points to be known across multiple cameras, a common 3D data environment can be created. A means for correlating between the RGBD images (RGB for the color at each pixel, for example, red, green, blue, and D of the distance the pixel is from the camera) is needed to derive common points. This can be done with a structured light projection that can be observed simultaneously by multiple cameras. This light projection can be performed, for example, in a sequence of points with each being displayed uniquely, or it can be performed with many points at a time where the point size and/or shape is used to differentiate between one another.

The surfaces observed by the multiple cameras can be expected to deform through natural processes as well as a result of surgical manipulation of the site. Thus, the multi-camera common points should be continuously updated in a timely manner because of the chance for the surfaces to deform during the time that a sequence of points is observed. As a result, either the sequenced projection needs to be faster than some expected threshold of deformation velocity or the multiplicity of simultaneous projected points approach may be used.

Since a sufficient number of common 3D points spanning the observable surgical site may be measured in all cameras, the relative pose of the cameras in relation to one another can be computed and used to allow the image data to be projected onto the commonly observed 3D surface. The individual cameras may need to be calibrated to account for optical path distortions as well as imager pose relative to that pathway.

With all these measurements and calibrations present, a common data fusion representation of the surgical site is generated. From this, a projected view from a desired virtual endoscope location can be generated to provide to the surgeon her desired viewpoint. This viewing location can be dynamically updated relative to the time-variant data fusion representation or the data fusion representation can be fixed in time or even recorded and played back while the camera viewpoint is manipulated to provide additional surgical site insight. Note also that permits multiple observers to view the surgical site from their own chosen viewpoint simultaneously.

Referring to FIG. 1, a robotic surgical system 1 in accordance with the present disclosure is shown generally as a robotic system 10, a processing unit 30, and a user interface 40. The robotic system 10 generally includes linkages or arms 12 and a robot base 18. The arms 12 movably support a tool 20 having an end effector 22, which is configured to act on tissue. The arms 12 each have an end 14 that supports tool 20. In addition, the ends 14 of the arms 12 may include an imaging device 16, 16B, for imaging a surgical site "S." The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16, 16B, positioned on the ends 14 of the arms 12 and/or include data captured by imaging devices that are positioned about the surgical theater (e.g., an imaging device positioned within the surgical site "S," an imaging device positioned adjacent the patient, imaging device 56 positioned at a distal end of an imaging linkage or arm 52). The imaging devices (e.g., imaging devices 16, 16B, 56) may capture visual images, infra-red images, ultrasound images, X-ray images, thermal images, and/or any other known real-time images of the surgical site "S." The imaging devices transmit captured imaging data to the processing unit 30, which creates three-dimensional images of the surgical site "S" in real-time from the imaging data and transmits the three-dimensional images to the display device 44 for display. It is contemplated that imaging device 56 may be an optical trocar or the like capable of capturing 2D/3D images in the visible spectrum of light, in the infrared spectrum, or in any other spectrum contemplated, as well as to be able to apply filtering and processing thereto to enhance the images/videos captured.

The user interface 40 also includes input handles 42 which are supported on control arms 43, which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include input devices (not shown) which allow the surgeon to manipulate (e.g., clamp, grasp, fire, open, close, rotate, thrust, slice, etc.) the end effectors 22 of the tools 20 supported at the ends 14 of the arms 12.

Each of the input handles 42 is movable through a predefined workspace to move the ends 14 of the arms 12 within a surgical site "S." The three-dimensional images on the display device 44 are orientated such that movement of the input handle 42 moves the ends 14 of the arms 12 as viewed on the display device 44. It will be appreciated that the orientation of the three-dimensional images on the display device may be mirrored or rotated relative to view from above the patient. In addition, it will be appreciated that the size of the three-dimensional images on the display device 44 may be scaled to be larger or smaller than the actual structures of the surgical site "S" permitting a clinician to have a better view of structures within the surgical site "S." As the input handles 42 are moved, the tools 20, and thus the end effectors 22, are moved within the surgical site "S" as detailed below. As detailed herein, movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

Figure 2:
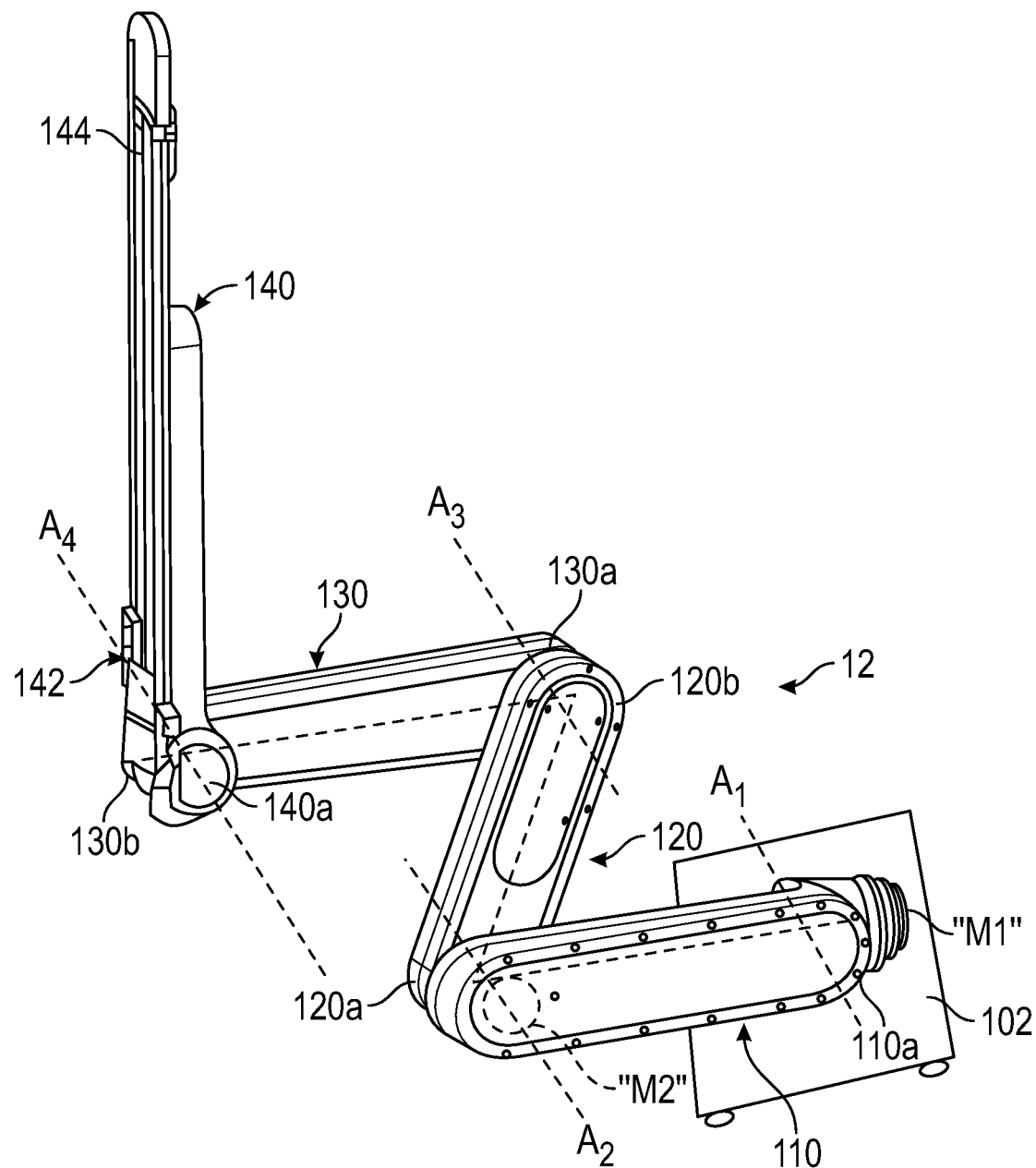
FIG. 2 is a perspective view of a linkage of the robotic system of FIG. 1.

With reference to FIG. 2, the robotic system 10 is configured to support the tool 20 (FIG. 1) thereon and to selectively move the tool 20 in a plurality of orientations relative to a small incision in a patient "P" (FIG. 1) while maintaining the tool 20 within the small incision. The arm 12 includes a plurality of elongate members or links 110, 120, 130, 140 pivotably connected to one another to provide varying degrees of freedom to the arm 12. In particular, the arm 12 includes a first link 110, a second link 120, a third link 130, and a fourth link 140.

The first link 110 has a first end 110a and a second end 110b. The first end 110a is rotatably coupled to a fixed structure. The fixed structure can be a movable cart 102 locked in position, a surgical table, a stanchion, an operating room wall, or other structure present in the operating room. A first motor "M1" is operably coupled to first end 110a to rotate the first link 110 about a first axis of rotation $A_1$ that passes through the first end 110a transverse to a longitudinal axis of the first link 110. The second end 110b of first link 110 has a second motor "M2" operably coupled to a first end of 120a of the second link 120 such that actuation of motor "M2" effects a rotation of the second link 120 relative to first link 110 about a second axis of rotation $A_2$ defined through the second end 110b of first link 110 and a first end 120a of second link 120. It is envisioned the second axis of rotation $A_2$ can be transverse to the longitudinal axis of the first link 110 and a longitudinal axis of the second link 120.

A second end 120b of the second link 120 is operably coupled to the first end 130a of the third link 130 such that the third link 130 rotates relative to the second link 120 about a third axis of rotation $A_3$ that passes through the second end 120b of the second link and the first end 130a of the third link 130. The third axis of rotation $A_3$ is parallel to the second axis of rotation $A_2$. Rotation of the second link 120 about the second axis of rotation $A_2$ affects rotation of the third link 130 about the third axis of rotation $A_3$ such that the first and third links 110, 130 maintain a substantially parallel relationship with one another.

A second end 130b of the third link 130 is operably coupled to a first end 140a of the fourth link 140. The fourth link 140 is rotatable relative to the third link 130 about a fourth axis of rotation $A_4$ that passes through the second end 130b of the third link 130 and the first end 140a of the fourth link 140.

Figure 3:
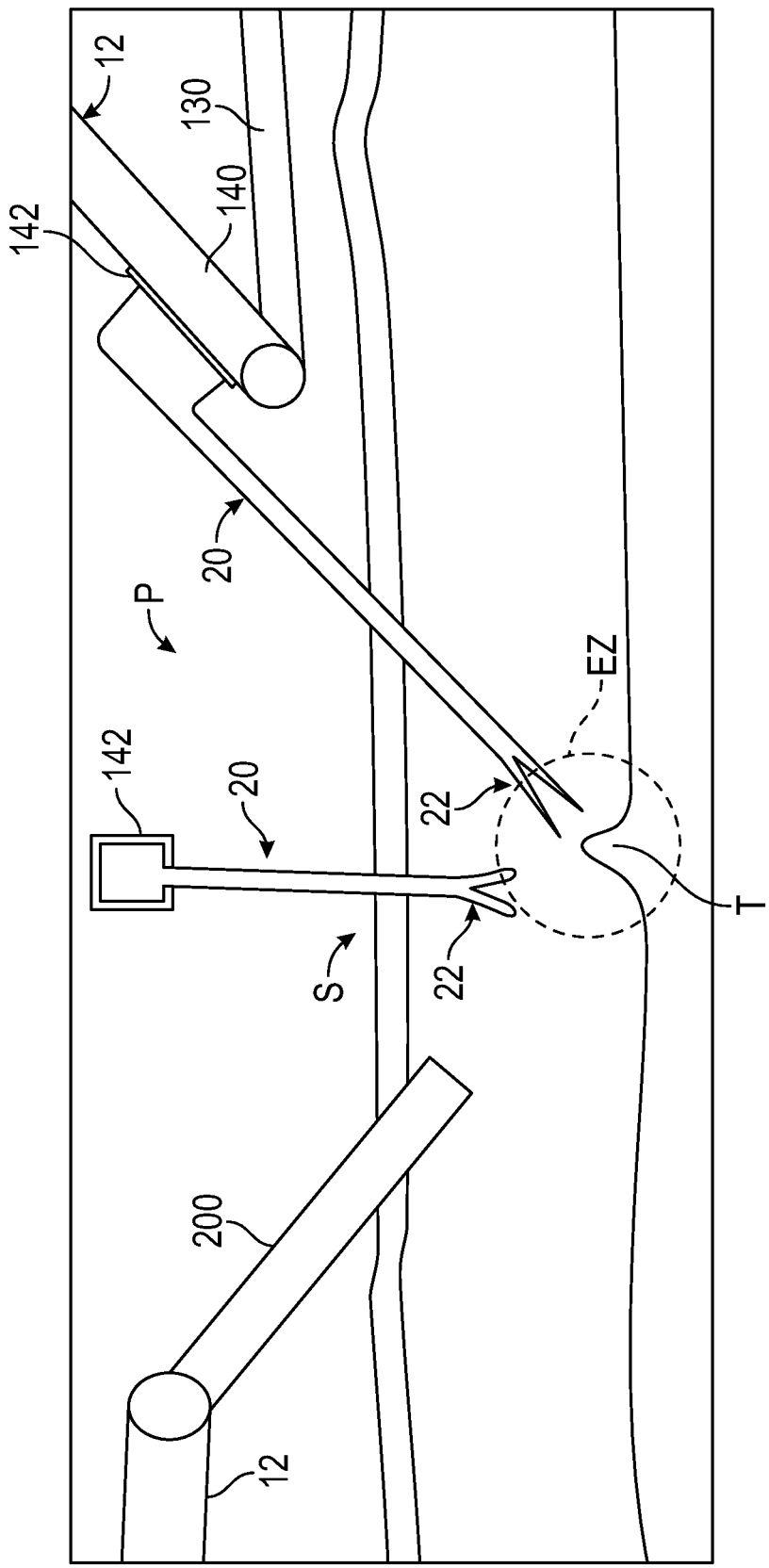
FIG. 3 is a schematic illustration of a surgical site with tools of the robotic system of FIG. 1 inserted therein.

With additional reference to FIG. 3, the fourth link 140 can be in the form of a rail that supports a slider 142. The slider 142 is slidable along an axis parallel to the longitudinal axis of the fourth link 140 and supports the tool 20.

During a surgical procedure, the robotic system 10 receives input commands from the user interface 40 to move the tool 20 such that the end effector 22 is moved to manipulate and/or act on tissue within the surgical site "S". Specifically, the links 110, 120, 130, 140 of the robot arm 12 are rotated relative to one another and the slider 142 is translated to position and orientate the tool 20 within the surgical site "S" in response to the input commands. To control the robot arm 12, the robotic system 10 calculates a desired tool pose of the tool 20 from the input commands, captures a tool pose of the tool 20, and manipulates the robot arm 12 to move the tool 20 to the desired tool pose. From the desired tool pose, the robotic system 10 calculates a required arm pose of the robot arm 12 to achieve the desired tool pose. The robot arm 12 then determines which links 110, 120, 130, 140 to manipulate to reach the required arm pose and thus, the desired tool pose of the tool 20 within the surgical site "S" in response to input captured by the user interface 40 (FIG. 1).

To determine the arm pose of the robot arm 12, the robot system 10 uses an imaging device or endoscope 200 positioned within the surgical site "S" to capture the position and orientation or tool pose of the tool 20 within the surgical site "S". As detailed herein below, the endoscope 200 is described as capturing the tool pose within the surgical site; however, it is contemplated that imaging devices can be used and that each one of the imaging devices can include a single or multiple lenses to capture two or three dimensional images.

The endoscope 200 can be stationary within the surgical site "S", can be manipulated by a clinician within the surgical theater, or can be attached to another robot arm 12 such that the position and orientation of the endoscope 200 can be manipulated during a surgical procedure. The robotic system 10 uses the endoscope 200 to visually capture the tool pose of the tool 20 within the surgical site "S" using known techniques. The tool 20 may include indicia to aid in capturing the tool pose, which may include, but are not limited to, using distinct colors, distinct markings, distinct shapes, or combinations thereof. The tool pose of the tool 20 is captured in a camera frame relative to the endoscope 200 and can be translated to a frame of the surgical site "S", a frame of the tool 20, a frame of the robot arm 12, or any other desired frame of reference. It is envisioned that it may be beneficial to translate the tool pose of the tool 20 to a fixed frame.

From the tool pose of the tool 20, the robotic system 10 can use known kinematics of the robot arm 12 to calculate an arm pose of the robot arm 12 starting from the tool pose of the tool 20 and working towards the first link 110. By calculating the arm pose of the robot arm 12 from tool pose of the tool 20, a solution to move the tool 20 to a desired tool pose within the surgical site "S" accounts for any deformations of the robot arm 12 or the tool 20 when under load. In addition, by calculating the arm pose from the tool pose, it is unnecessary to know the position of the fixed structure (e.g., movable cart 102), to which the first link 110 (FIG. 2) of the arm 12 is coupled, to determine a solution to move the tool 20 to the desired tool pose. In calculating the solution, the robotic system 10 accounts for any possible collisions of the arm 12 with other arms 12, clinicians within the surgical theater, the patient, or other structures within the surgical theater. Further, by calculating the tool pose and/or the arm pose in a common frame, e.g., the camera frame of a single endoscope, the poses of the tools and/or arms can be computed at the same time by using the kinematics of each of the arms, e.g., arm 12, to calculate the locations of the links, e.g., link 110, to estimate possible collisions of the arm 12.

It is contemplated that the robot system 10 can be used to simultaneously capture the tool pose of multiple tools 20 with the endoscope 200. By capturing the tool pose of multiple tools 20, the interaction of the tools 20 and the end effectors 22 of the tools 20 can be controlled with high precision. This high precision control can be used to complete automated tasks; for example, suturing tissue. It is envisioned that by using a single endoscope 200 to capture the tool poses of multiple tools 20, the speed and accuracy of automated tasks can be increased by reducing the need to translate the high precision tool poses from a camera frame to another frame for the duration of the automated task.

It is contemplated that more than one camera and/or endoscope 200 can be used to simultaneously capture the tool pose of the tool 20 within the surgical site "S." It will be appreciated that when multiple cameras are used that it may be beneficial to translate the position and orientation of the tool 20 to a frame other than a frame defined by one of the cameras.

It is contemplated that determining the arm pose from the captured tool pose allows for determining the position of movable carts 102 supporting each of the arms 12 from the captured tool pose and the kinematics of the arms 12. After the surgical procedure is completed, the efficiency of the surgical procedure can be determined, and the position of the movable carts 102 recorded. By comparing the position of movable carts 102 during surgical procedures with high efficiency ratings, a guide or recommended locations of the movable carts 102 for a given procedure can be provided to increase the efficiency of future surgical procedures. Increased efficiency of surgical procedures can reduce cost, surgical time, and recovery time while improving surgical outcome.

Figure 4:
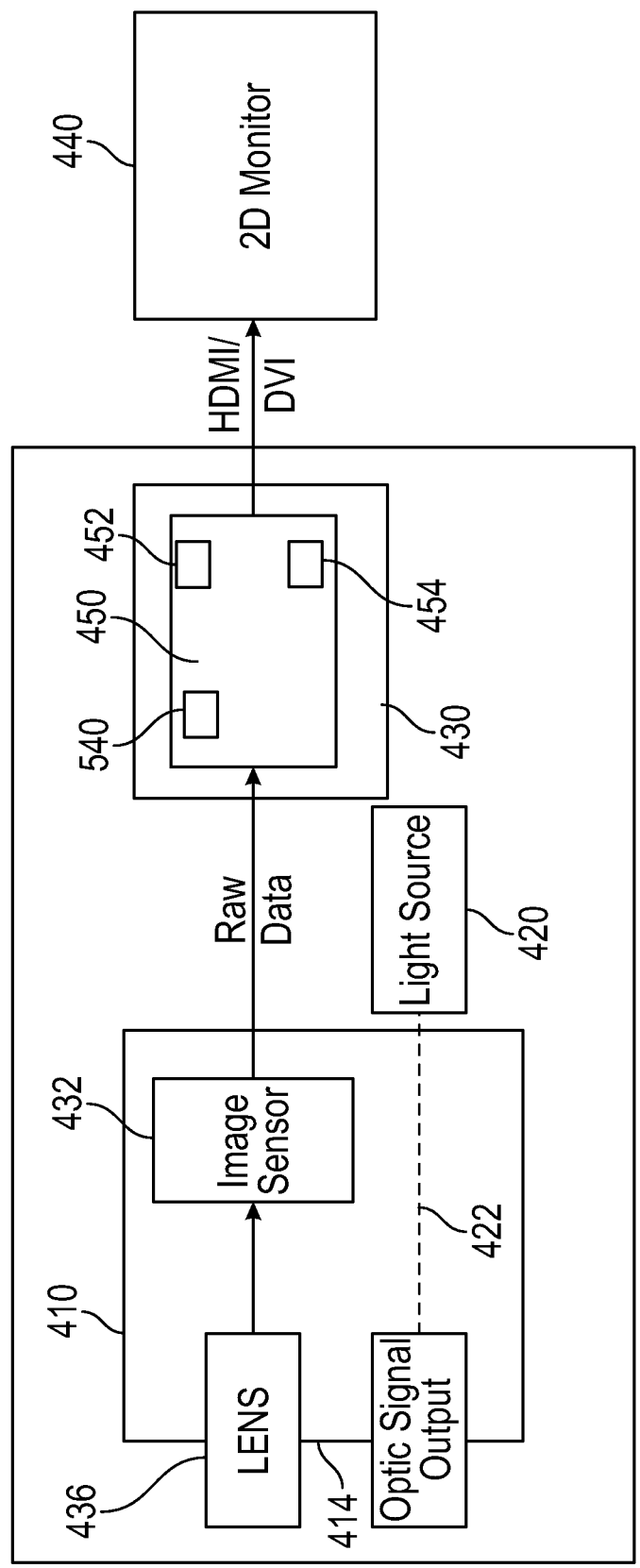
FIG. 4 is a schematic configuration of the visualization or imaging system in accordance with an embodiment of the disclosure.

Referring to FIG. 4, there is shown a schematic configuration of an endoscope system, which may be the imaging devices 16, 16B of FIG. 1, or may be a different type of system (e.g., visualization system, etc.). The system, in accordance with the disclosure, includes an imaging device 410, a light source 420, a video system 430, and a display device 440. The light source 420 is configured to provide light to a surgical site through the imaging device 410 via the fiber guide 422. The distal end 414 of the imaging device 410 includes an objective lens 436 for receiving or capturing the image at the surgical site. The objective lens 436 forwards or transmits the image to the image sensor 432. The image is then communicated to the video system 430 for processing. The video system 430 includes an imaging device controller 450 for controlling the endoscope and processing the images. The imaging device controller 450 includes a processor 452 connected to a computer-readable storage medium or a memory 454 which may be a volatile type memory, such as RAM, or a non-volatile type memory, such as flash media, disk media, or other types of memory. In various embodiments, the processor 452 may be another type of processor such as, without limitation, a digital signal processor, a microprocessor, an ASIC, a graphics processing unit (GPU), field-programmable gate array (FPGA), or a central processing unit (CPU).

In various embodiments, the memory 454 can be random access memory, read only memory, magnetic disk memory, solid state memory, optical disc memory, and/or another type of memory. In various embodiments, the memory 454 can be separate from the imaging device controller 450 and can communicate with the processor 452 through communication buses of a circuit board and/or through communication cables such as serial ATA cables or other types of cables. The memory 454 includes computer-readable instructions that are executable by the processor 452 to operate the imaging device controller 450. In various embodiments, the imaging device controller 450 may include a network interface 540 to communicate with other computers or a server.

Figure 5:
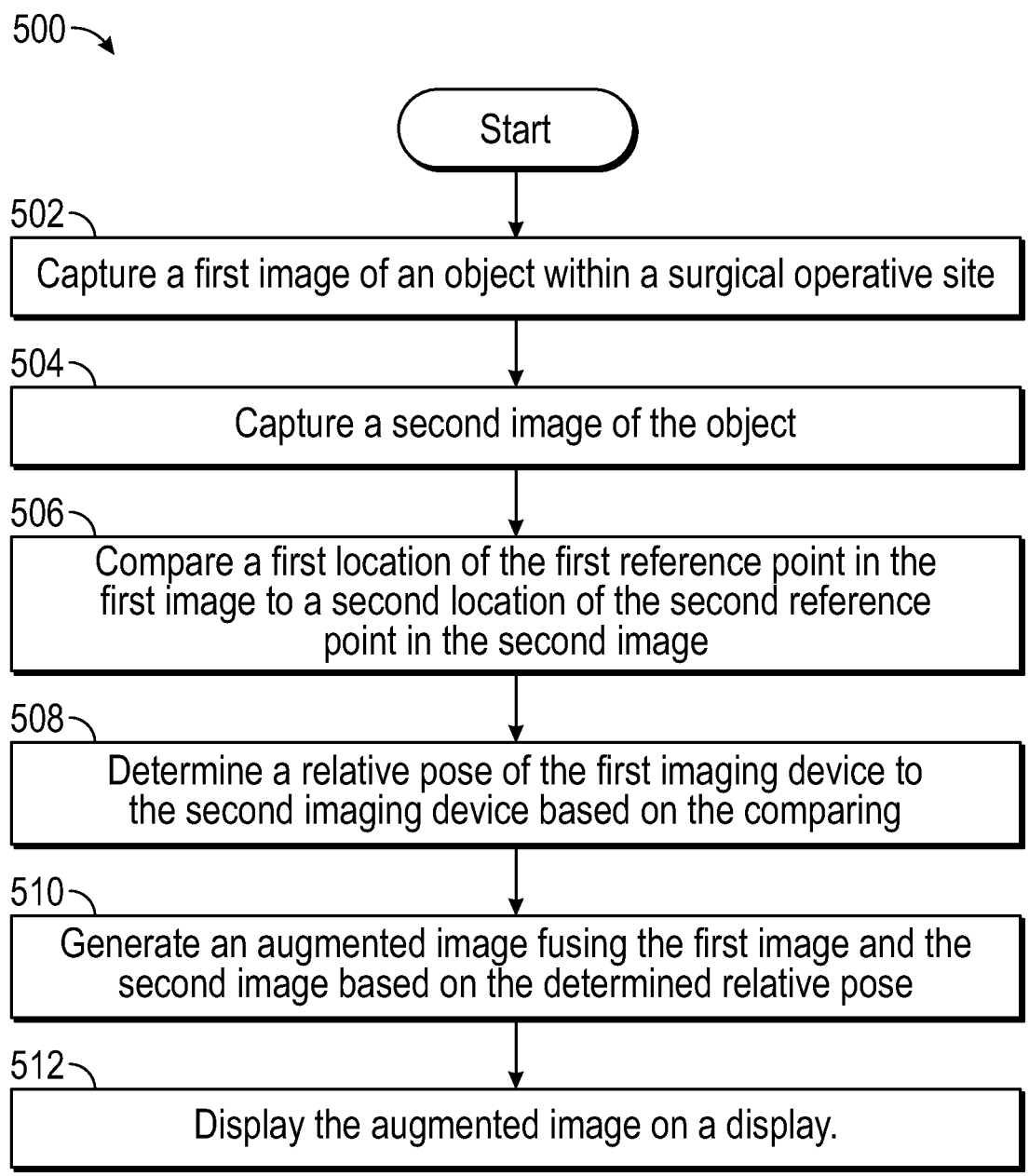
FIG. 5 is a flowchart of a method for mapping and fusion of endoscopy images in accordance with an exemplary embodiment of the disclosure.

With reference to FIG. 5, the flow diagram includes various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by one or more video system 430, but those skilled in the art will appreciate that the video system 430 is exemplary. In various embodiments, the disclosed operations can be performed by another component, device, or system. In various embodiments, the video system 430 or other component/device performs the actions or tasks via one or more software applications executing on a processor. In various embodiments, at least some of the operations can be implemented by firmware, programmable logic devices, and/or hardware circuitry. Other implementations are contemplated to be within the scope of the disclosure.

Referring now to FIG. 5, there is shown an operation for mapping and fusing endoscopy images. In various embodiments, the operation of FIG. 5 can be performed by a robot system 10 described above herein. In various embodiments, the operation of FIG. 5 can be performed by another type of system and/or during another type of procedure. The following description will refer to a robot system, but it will be understood that such description is exemplary and does not limit the scope and applicability of the disclosure to other systems and procedures.

Initially, at step 502, a first image of a surgical site is captured via the objective lens 436 and forwarded to the image sensor 432 of a first imaging device 16 of robot system 10. At step 504, a second image of the surgical site is captured via the objective lens 436 and forwarded to the image sensor 432 of a second imaging device 16B of robot system 10.

The image may include a first light (e.g., infrared) and a second light (e.g., visible light). For example, two light sources may be present to illuminate the surgical site for the robot system 10. One light source may be a broad-spectrum white light whose wavelengths would be blocked so that they do not go above the visible range of about 740 nm. The other light source may be purely near-infrared, typically anywhere between about 780 nm and 850 nm. It is contemplated that the first light and the second light may be used simultaneously or in any order.

The term "image" as used herein may include still images or moving images (for example, video). The first image includes a first light (e.g., infrared). The second image includes a second light (e.g., visible light). For example, two light sources may be present to illuminate the surgical site for the robot system 10. One light source may be a broad-spectrum white light whose wavelengths would be blocked so that they do not go above the visible range of about 740 nm. The other light source may be purely near-infrared, typically anywhere between about 780 nm and 850 nm. It is contemplated that the first light and the second light may be used simultaneously or in any order. In systems, the image sensor 432 of imaging device 116, 16B, may include CMOS sensors.

In systems, when indocyanine green (ICG)-based fluorescence-based imaging is needed, the system may include a mode that would allow the visible light and infrared light (IR) lighting to be on simultaneously with the visible light component considerably reduced in its illumination intensity. ICG based imaging uses near-infrared light to add contrast to tissue imaging during surgical procedures.

In systems, the captured image is communicated to the video system 430 for processing. For example, during an endoscopic procedure, a surgeon may cut tissue with an electrosurgical instrument. When the first image and the second image are captured, they may include objects such as the tissue and/or the instrument.

The object may further include a reference point configured to aid in the lining up of multiple endoscopic images. The reference point may be projected onto the object using structured light. Structured light is the process of projecting a known pattern (often grids or horizontal bars) on to a scene. The way that these deform when striking surfaces allows vision systems such as the robot system 10 to calculate the depth and surface information of the objects in the scene. Invisible (or imperceptible) structured light uses structured light without interfering with other computer vision tasks for which the projected pattern will be confusing. Example methods include the use of IR light or of extremely high frame rates alternating between two exact opposite patterns. In various embodiments, the structured light may include time-sequenced and/or geometrically unique structured light projection.

The IR structured light reference points on the objects may be visible in this mode, and the primary focus is on when tissue shows it is perfused. In various embodiments, the IR structured light reference points may be dimmer relative to the perfusion. The system may retune the IR wavelength for the IR structured light reference points. For example, the ICG IR light could be at 785 nm, whereas the IR structured light could be above 850 nm. In this way, the structured light IR light would not stimulate the ICG and vice versa. In various embodiments, the imaging device 16, 16B, and/or robot system 10 may include multiple IR sources.

For example, the reference point may be located on the shaft of an instrument or on an organ. The reference point may include geometric shapes, or for example, a logo, a QR code, a texture, a dot pattern, and/or a unique identifier.

CMOS imagers which may be used in endoscopes are sensitive to IR and usually have filters to block from receiving this to prevent the image from being skewed by light not visible to the human eye. Since there is generally no light present within the body, all illumination needs to be added by the endoscope system, e.g., it is not natural light, which contains IR. If the IR wavelength needed for the structured light is tuned to the same one used for activating indocyanine green dye (ICG), which may be used to observe perfusion during surgery, then the same ICG capability that may be built into the endoscope can be leveraged. For example, this wavelength may be in the range of about 785 nm. The video system 430 accesses the first and second images for further processing.

At step 506, the video system 430 compares a first location of the first reference point in the first image to a second location of the second reference point in the second image. For example, the object in the first image may be at a slightly different location than the same object in the second image because of a different relative pose between the first imaging device and the second imaging device.

At step 508, the video system 430 determines a relative pose of the first imaging device to the second imaging device based on the comparing. For example, the video system 430 may determine that the first imaging device is a few centimeters to the left relative to the second imaging device based on the comparison. The first image may include distance information for each pixel of the first image and the second image. The relative pose of the first imaging device may be based on the distance information in the first image. The relative pose of the second imaging device may be based on the distance information in the second image.

At step 510, the video system 430 generates an augmented image fusing the first image and the second image based on the determined relative pose. The visible light image may include color information, and the IR image may include a greyscale image. When fusing the two images, some blending may be performed. Some areas of the data fusion representation may include only a single imaging device's information. For example, in the augmented image, an organ may only include the color information and not the greyscale information, yet the remainder of the image would be a blend of the color information and the greyscale information.

For example, if the multiple cameras whose depth enabled images are to be fused into the surgical site representation are of widely varying imaging modalities, say visible light producing full color in one and MR yielding a greyscale image in another, accommodation should be made to blend these. Much like with the common variation in transparency-based rendering of MR information on top of visible light, some appropriate blending must be done. There can be an aspect where some areas of the data fusion representation will only have a single camera's information projected upon it so that it will not have blended information. Still, the transition from blended to single source may be rendered in an appropriate manner to lessen cognitive dissonance when the viewing camera points at those areas.

When generating the augmented image, the video system 430 may determine a first optical path distortion of the first imaging device and a second optical path distortion of the second imaging device. The video system 430 may then process the first image based on the first optical path distortion to match the second optical path distortion.

The video system 430 may generate a virtual image viewpoint. The video system 430 may determine a virtual imaging device viewpoint based on an input by a clinician, and the generated augmented image may be based on the virtual imaging device viewpoint. For example, a projected view from a desired virtual endoscope location can be generated to provide a clinician his desired viewpoint At step 512, the video system 430 displays the augmented image on a display for the operator to see. In various embodiments, the video system 430 may perform tracking of the object based on the detected object based on the first and second reference points. For example, stereoscopic viewing can also be provided by creating two synthetic cameras instead of one which are separated by the desired stereo base distance. The resulting two images can be displayed on a typical stereoscopic monitor using standard techniques.

The flow diagram includes various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by one or more video system 430, but those skilled in the art will appreciate that the video system 430 is exemplary. In various embodiments, the disclosed operations can be performed by another component, device, or system. In various embodiments, the video system 430 or other component/device performs the actions or tasks via one or more software applications executing on a processor. In various embodiments, at least some of the operations can be implemented by firmware, programmable logic devices, and/or hardware circuitry. Other implementations are contemplated to be within the scope of the disclosure.

In various embodiments, the operation of FIG. 5 can be performed by a robot system 10 described above herein. In various embodiments, the operation can be performed by another type of system and/or during another type of procedure. The following description will refer to a robot system, but it will be understood that such description is exemplary and does not limit the scope and applicability of the disclosure to other systems and procedures.

Initially, at step 602, a first image of a surgical site is captured via the objective lens 436 and forwarded to the image sensor 432 of a first imaging device 16 of robot system 10. At step 604, a second image of the surgical site is captured via the objective lens 436 and forwarded to the image sensor 432 of a second imaging device 16B of robot system 10. For example, the first imaging device may be a wide field of view 2D imaging device located on/in a trocar.

The second imaging device may be, for example, a stereographic imaging device such as an endoscope. The first and the second imaging devices may have different viewpoints from each other. It is contemplated that the first imaging device and the second imaging device may be any combination of imaging devices (e.g., two 2D device, a 2D and a stereoscopic device, two stereoscopic devices, etc.). It is further contemplated that more than two imaging devices may be used for image capture.

Next, at step 606, the method segments the first and second images to extract a known reference (for example, a surgical tool, or an imaging device). Image segmentation is the process of partitioning an image into multiple segments (e.g., sets of pixels known as image objects) and assigning a label to every pixel in an image such that pixels with the same label share certain characteristics. Image segmentation may be used for object detection in images, for example, to extract a known reference (e.g., structured light, an organ, or a surgical tool) in an image of a surgical operative site.

In various embodiments, the first image may include the first location of the first imaging device, and the second image may include the location of the second imaging device. The location information may be based on, for example, a location sensor (e.g., GPS, RFID), or a manual entry of the location of the imaging device. The first imaging device has a first viewpoint of the surgical operative site, and the second imaging device may have a second viewpoint of the surgical operative site different from the first viewpoint. In various embodiments, the known reference object may include structured light projected on the surgical operative site. A second light source may be used to project the structured light on the surgical site. The structured light may be captured in the first and second image and may be used, for example, for the comparison of the locations of the images.

Next, at step 608, the method determines the relative location of each of the imaging devices based on the known reference object (e.g., a first relative location and a second relative location, respectively).

Next, at step 610, the method constructs a 3D model based on the determined first relative location of the first imaging device and the determined second relative location of the second imaging device.

When constructing the 3D model, the method may further include determining a virtual imaging device viewpoint, generating a virtual viewpoint of the 3D model based on the virtual imaging device. For example, the virtual viewpoint of the 3D model from a desired virtual endoscope location can be generated to provide to the surgeon their desired viewpoint. This viewing location can be dynamically updated relative to a time-variant 3D model representation, or the 3D model representation can be fixed in time or even recorded and played back while the virtual imaging device viewpoint is manipulated to provide additional surgical site insight. Note also that permits multiple observers to view the surgical site from their own chosen viewpoint simultaneously. Note that stereoscopic viewing can also be provided by creating two virtual imaging device locations instead of one which are separated by the desired stereo base distance. The resulting two images can be displayed on a typical stereoscopic monitor using standard techniques. Next, at step 612, the method displays the stereoscopic virtual imaging device viewpoint.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RANI), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the disclosure. Various alternatives and modifications can be devised by those skilled in the art without departing from the disclosure. Accordingly, the disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for mapping and fusing endoscopy images, comprising:
    a display;
    a light source configured to provide light within a surgical operative site, the light source configured to produce a first light including an infrared (IR) band and a second light configured to produce a visible band;
    a first imaging device configured to acquire images from the surgical operative site;
    a second imaging device configured to acquire images from the surgical operative site; and
    an imaging device control unit configured to control the first imaging device and the second imaging device, the control unit including:
        a processor; and
        a memory storing instructions thereon, which, when executed by the processor, cause the system to:
            capture a first image of an object within a surgical operative site, by the first imaging device, the first image including the first light radiating from the object, and a first reference point;
            capture a second image of the object, by the second imaging device, the second image including the second light radiating from the object, and a second reference point;
            compare a first location of the first reference point in the first image to a second location of the second reference point in the second image;
            determine a relative pose of the first imaging device to the second imaging device based on the comparing;
            generate an augmented image fusing the first image and the second image based on the determined relative pose; and
            display the augmented image on the display.

2. The system of claim 1, wherein the light source configured to produce a first light including an infrared (IR) band and a second light configured to produce a visible band.

3. The system of claim 1, wherein the first reference point includes a structured light, and wherein the second reference point includes a structured light.

4. The system of claim 3, wherein generating the augmented image further includes:
    determining a virtual imaging device viewpoint, and wherein generating the augmented image is further based on the virtual imaging device viewpoint.

5. The system of claim 1, wherein generating the augmented view further includes:
    determining a first optical path distortion of the first imaging device and a second optical path distortion of the second imaging device; and processing the first image based on the first optical path distortion to match the second optical path distortion.

6. The system of claim 1, wherein the instructions, when executed, further cause the system to perform tracking of the object based on the first reference point and the second reference point.

7. The system of claim 1, wherein the first reference point and the second reference point include at least one of a logo, a QR code, a texture, a dot pattern, or a unique identifier.

8. The system of claim 1, wherein the first image includes a first distance information for each pixel of the first image,
wherein the second image includes a second distance information for each pixel of the second image, and
wherein the relative pose of the first imaging device is further based on the first distance information and the second distance information.

9. The system of claim 1, wherein the generating the augmented image further includes a portion of the first image which includes the object to represent the object in the augmented image, and a remaining portion of the augmented image includes a fusion of the first image and the second image.

\* \* \* \* \*